(12) United States Patent
Shintaku et al.

(10) Patent No.: US 6,369,266 B1
(45) Date of Patent: Apr. 9, 2002

(54) PROCESS FOR PRODUCING TERT-BUTYL 4'-METHYL-2-BIPHENYLCARBOXLATE

(75) Inventors: Tetsuya Shintaku; Kiyoshi Sugi; Tadashi Katsura; Nobushige Itaya, all of Osaka (JP)

(73) Assignee: Sumika Fine Chemicals, Co.,Ltd., Osaka (JP)

( * ) Notice: Subject to any disclaimer, the term of this patent is extended or adjusted under 35 U.S.C. 154(b) by 0 days.

(21) Appl. No.: 09/530,882

(22) Filed: May 8, 2000

(30) Foreign Application Priority Data

Nov. 14, 1997 (JP) .............................................. 9-313931
Jul. 8, 1998 (JP) ........................................... 10-193034

(51) Int. Cl.[7] .......................... C07C 69/76; C07C 63/33
(52) U.S. Cl. ....................................... 560/102; 562/492
(58) Field of Search ........................... 560/102; 562/492

(56) References Cited

FOREIGN PATENT DOCUMENTS

| EP | 0537937 A2 | 4/1993 |
|---|---|---|
| JP | A61790 | 1/1994 |
| JP | 1077244 | 3/1998 |
| WO | A1918888 | 12/1991 |

OTHER PUBLICATIONS

"Lectures on Experimental Chemicatry", vol. 14, No. 4, pp. 12–13 (1992), in Japanese.
Partial English language translation of "Lectures on Experimental Chemistry", vol. 14, 4th Edition, Organic Synthesis IV, 1992.
Chemical Abstracts, vol. 119; 271196s (1993).
Harrison and Harrison, "Compendium of Organic Synthetic Methods". 1971; John Wiley and Sons, Inc. pp. 64 and 274.

*Primary Examiner*—Sreeni Padmanabhan
*Assistant Examiner*—Sikarl A. Witherspoon
(74) *Attorney, Agent, or Firm*—Birch, Stewart, Kolasch & Birch, LLP

(57) ABSTRACT

A process for preparing tert-butyl 4'-methyl-2-biphenylcarboxylate characterized in that 4'-methyl-2-biphenylcarboxylic acid is reacted with isobutene in the presence of an acid catalyst. According to the present invention, tert-butyl 4'-methyl-2-biphenylcarboxylate having high quality can be conveniently and industrially advantageously prepared in a high yield under mild reaction conditions such as ambient temperatures without complicated procedures or any hazardous solvents.

6 Claims, No Drawings

PROCESS FOR PRODUCING TERT-BUTYL 4'-METHYL-2-BIPHENYLCARBOXLATE

This application is the national phase under 35 U.S.C. §371 of PCT International Application No. PCT/JP98/05099 which has an International filing date of Nov. 13, 1998, which designated the United States of America.

TECHNICAL FIELD

The present invention relates to a process for preparing tert-butyl 4'-methyl-2-biphenylcarboxylate. More particularly, the present invention relates to a process for preparing tert-butyl 4'-methyl-2-biphenylcarboxylate, which is useful as an intermediate of pharmaceuticals such as antihypertensives.

BACKGROUND ART

Conventionally, there have been known processes for preparing tert-butyl 4'-methyl-2-biphenylcarboxylate, including (A) a process of reacting p-methylphenylzinc chloride with 2-tert-butoxycarbonyliodobenzene in the presence of $NiCl_2(Ph[phenyl\ group,\ hereinafter\ referred\ to\ the\ same]_3P)_2$ as a catalyst (Japanese Patent Laid-Open No. Hei 6-1790); and (B) a process of reacting 4'-methyl-2-biphenylcarboxylic acid with isobutene in anhydrous ether in the presence of concentrated sulfuric acid as a catalyst (Japanese Unexamined Patent Publication No. Hei 5-506443).

However, there are some defects in the process (A) such that complicated procedures are necessitated in the preparation of p-methylphenylzinc chloride as a starting material, since there is a necessity to prepare the p-methylphenylzinc chloride at an extremely low temperature of −78° C., and that relatively expensive reagents such as 2-tert-butoxycarbonyliodobenzene and $NiCl_2(Ph_3P)_2$ are needed.

In the process (B), since an ether is used, there has been desired to develop a process in which a highly hazardous solvent such as the ether is not used.

Accordingly, in recent years, there have been desired to establish a process capable of conveniently and industrially advantageously preparing tert-butyl 4'-methyl-2-biphenylcarboxylate in a high yield.

An object of the present invention is to provide a process capable of easily preparing tert-butyl 4'-methyl-2-biphenylcarboxylate having high quality in a high yield without requiring complicated procedures or any hazardous solvents.

DISCLOSURE OF INVENTION

According to the present invention, there is provided a process for preparing tert-butyl 4'-methyl-2-biphenylcarboxylate, characterized in that 4'-methyl-2-biphenylcarboxylic acid is reacted with isobutene in the presence of an acid catalyst.

BEST MODE FOR CARRYING OUT THE INVENTION

According to the present invention, tert-butyl 4'-methyl-2-biphenylcarboxylate can be prepared by reacting 4'-methyl-2-biphenylcarboxylic acid with isobutene in the presence of an acid catalyst.

4'-Methyl-2-biphenylcarboxylic acid, a starting material in the present invention, can be prepared by hydrolyzing 2-cyano-4'-methylbiphenyl in a glycol in the presence of an alkali.

The alkali includes, for instance, sodium hydroxide, potassium hydroxide, and the like.

It is desired that the amount of the alkali used is usually 1 to 4 mol, preferably 2 to 3 mol, per one mol of the above-mentioned 2-cyano-4'-methylbiphenyl.

The hydrolysis of the above-mentioned 2-cyano-4'-methylbiphenyl can be carried out by dissolving 2-cyano-4'-methylbiphenyl and an alkali in a glycol to give a solution, and thereafter stirring the solution with heating as occasion demands.

In the present invention, the glycol is used as a solvent. It is preferable that the glycol is mixed with water from the viewpoint of speedily progressing the reaction. When the glycol is mixed with water, the amount of water used is not limited to specified ones, and it is desired that the amount of water is usually 1 to 100 parts by weight or so, preferably 5 to 50 parts by weight or so, based on 100 parts by weight of the glycol.

The above-mentioned glycols include, for instance, ethylene glycol, propylene glycol, butanediol, diethylene glycol, and the like. Among them, glycols having high boiling points (198° to 215° C.), such as ethylene glycol and propylene glycol, are preferable.

It is preferable to adjust the amount of the glycol used so that the amount of the above-mentioned 2-cyano-4'-methylbiphenyl is 1 to 100 parts by weight or so, preferably 25 to 50 parts by weight or so, based on 100 parts by weight of the solvent.

The hydrolysis of the above-mentioned 2-cyano-4'-methylbiphenyl can be usually carried out in the range of 100° to 200° C. The higher the temperature is, the reaction completes in a shorter period of time.

The atmosphere in which 2-cyano-4'-methylbiphenyl is hydrolyzed is not limited to specified ones. Usually, the atmosphere may be air, or an inert gas such as nitrogen gas or argon gas. In addition, it is preferable that the reaction pressure is usually normal pressure to 10 $kgf/cm^2$ (gauge pressure, hereinafter referred to the same) or so. In the present invention, it is preferable to carry out hydrolysis with removing ammonia gas formed by the reaction from the reaction system.

The termination of reaction can be confirmed, for instance, by high-performance liquid chromatography, and the like.

After the termination of reaction, desired 4'-methyl-2-biphenylcarboxylic acid can be isolated by, for instance, adding water, toluene, or the like to the reaction solution, removing its neutral portion by extraction; further adding hydrochloric acid to release the resulting product; and collecting the product as crystals by filtration. Further, 4'-methyl-2-biphenylcarboxylic acid having a higher purity can be obtained by dissolving the resulting crystals in toluene, or the like, and recrystallizing the crystals therefrom.

tert-Butyl 4'-methyl-2-biphenylcarboxylate can be prepared by reacting the thus obtained 4'-methyl-2-biphenylcarboxylic acid with isobutene in the presence of an acid catalyst.

The amount of isobutene which is used in the reaction with 4'-methyl-2-biphenylcarboxylic acid is not limited to specified ones. It is desired that the amount of isobutene is at least 1.5 mol, preferably at least 2 mol, more preferably at least 3 mol, from the viewpoint of reactivity, and at most 10 mol, preferably at most 7 mol, from the viewpoint of economics, per one mol of 4'-methyl-2-biphenylcarboxylic acid.

As the acid catalyst, sulfuric acid, sulfonic acids and phosphorus halides are preferable from the viewpoints of reactivity and economics.

The sulfonic acid includes, for instance, methanesulfonic acid, p-toluenesulfonic acid, and the like. Also, the phosphorus halide includes, for instance, phosphorus oxytrichloride, phosphorus trichloride, phosphorus pentachloride, and the like. Among these phosphorus halides, phosphorus oxytrichloride and phosphorus trichloride are preferable from the viewpoint of reactivity. Incidentally, it is preferable that sulfuric acid is usually a concentrated sulfuric acid having a concentration of 96 to 98% by weight.

It is desired that the amount of the acid catalyst is at least 0.1 mol, preferably at least 0.2 mol, from the viewpoint of reactivity, and at most 1.2 mol, preferably at most 1.1 mol, from the viewpoint of economics, per one mol of 4'-methyl-2-biphenylcarboxylic acid.

In the present invention, when sulfuric acid is used as an acid catalyst, it is preferable that 4'-methyl-2-biphenylcarboxylic acid is reacted with isobutene in the presence of a dehydrating agent. Incidentally, although the dehydrating agent is not particularly necessary when a sulfonic acid, a phosphorus halide, or the like is used as an acid catalyst, the dehydrating agent may be used if desired.

The dehydrating agent includes, for instance, anhydrous magnesium sulfate, and the like. The anhydrous magnesium sulfate can be preferably used from the viewpoint of reactivity.

It is desired that the amount of the dehydrating agent used is at least 0.1 mol, from the viewpoint of reactivity, and at most 3 mol, preferably at most 2 mol, from the viewpoint of economics, per one mol of 4'-methyl-2-biphenylcarboxylic acid.

In the present invention, when the reaction is carried out by using sulfuric acid as an acid catalyst, 4'-methyl-2-biphenylcarboxylic acid can be reacted with isobutene, for instance, by mixing the acid catalyst, the dehydrating agent, and a solvent mentioned below, adding 4'-methyl-2-biphenylcarboxylic acid to the resulting mixture, and introducing isobutene gas thereto, and the like.

Also, when the reaction is carried out using a sulfonic acid or a phosphorus halide as an acid catalyst, 4'-methyl-2-biphenylcarboxylic acid can be reacted with isobutene, for instance, by mixing 4'-methyl-2-biphenylcarboxylic acid with a solvent mentioned below, adding the phosphorus halide to the resulting mixture, and introducing isobutene gas thereto, and the like. When the reaction is carried out using a phosphorus halide as an acid catalyst, its ability as an acid catalyst can be adjusted by adding water. It is desired that the amount of water added at this stage is 0.1 to 1.2 mol, preferably 0.5 to 1.0 mol, per one mol of the phosphorus halide, from the viewpoint of reactivity.

Incidentally, it is preferable that the amount of isobutene gas used is adjusted so that the amount of isobutene used in the reaction can be the amount as mentioned above.

In the present invention, a solvent can be used in the reaction. The solvent includes, for instance, hydrocarbon solvents such as cyclohexane and toluene; halogenated solvents such as dichloromethane and dichloroethane, and the like. It is preferable that the amount of the solvent used can be adjusted so that the amount of 4'-methyl-2-biphenylcarboxylic acid can be usually 2 to 70 parts by weight or so, based on 100 parts by weight of the solvent.

The reaction temperature of 4'-methyl-2-biphenylcarboxylic acid with isobutene cannot be absolutely determined because the reaction temperature can differ depending upon the presence or absence of a dehydrating agent, and the like. For instance, when the reaction is carried out in the absence of a dehydrating agent, it is desired that the above-mentioned reaction temperature is usually 0° to 40° C., preferably 20° to 30° C. Also, for instance, when anhydrous magnesium sulfate or the like is used as a dehydrating agent, it is desired that the above-mentioned reaction temperature is usually 0° to 45° C., preferably 15° to 35° C., because magnesium sulfate releases its crystal water at about 48° C., thereby losing its dehydration ability.

The reaction time cannot be absolutely determined because the reaction time can differ depending upon reaction conditions such as reaction temperature. The reaction time can be a period of time necessary for completing the reaction. The reaction time is usually from 1 to 24 hours or so. Incidentally, the termination of the reaction can be confirmed by means of, for instance, high-performance liquid chromatography (HPLC), and the like.

The thus obtained reaction product can be isolated, for instance, by adding water to the reaction solution after the termination of the reaction, sufficiently stirring the solution to allow phase separation, thereafter washing the organic layer with an aqueous sodium hydroxide, or the like, and concentrating the organic layer by distilling off the organic solvent.

tert-Butyl 4'-methyl-2-biphenylcarboxylate obtained according to the present invention can be preferably used as an intermediate of pharmaceuticals such as antihypertensives.

Next, the present invention will be more specifically described on the basis of Examples, without intending to restrict the scope or spirit of the present invention thereto.

EXAMPLE I-1

A 300-ml four-neck flask equipped with a thermometer and a reflux condenser was charged with 88.76 g of ethylene glycol, 44.38 g (229.7 mmol) of 2-cyano-4'-methylbiphenyl and 18.38 g (459.4 mmol) of sodium hydroxide, and the resulting mixture was stirred and then heated.

The resulting reaction solution was stirred at 170° C. for 8 hours, and then cooled to 90° C. To this reaction solution was added dropwise 177.5 g of water. After the completion of dropwise addition, the mixture was stirred for 30 minutes. To this mixture was added 66.6 g of toluene, and 52.64 g (505.3 mmol) of 35% hydrochloric acid was further added dropwise. The temperature inside the flask was raised to 75° C. to dissolve the resulting product in toluene and form into two layers. After the solution was allowed to stand to separate into layers, the lower aqueous layer was removed therefrom. The toluene layer was dehydrated over anhydrous magnesium sulfate, and then gradually cooled to allow sedimentation of white crystals of 4'-methylbiphenyl-2-carboxylic acid. The temperature was lowered to 0° C., and its temperature was maintained for one hour, and then the crystals were filtered. After the crystals were washed with 20 g of toluene at 0° C., the crystals were air-dried to give 44.1 g of white crystals of 4'-methylbiphenyl-2-carboxylic acid (yield: 90.4% based on 2-cyano-4'-methylbiphenyl, purity: 99.9%). The resulting white crystals had a melting point of 150.1° C.

EXAMPLE I-2

A 300-ml four-neck flask equipped with a thermometer and a reflux condenser was charged with 95 g of ethylene glycol, 5 g of water, 50 g (0.259 mol) of 2-cyano-4'-methylbiphenyl and 20.7 g (0.517 mol) of sodium hydroxide, and the resulting mixture was mixed and then heated.

The resulting reaction solution was stirred at 150° C. for 10 hours, and then cooled to 90° C. To this reaction mixture was added dropwise 185 g of water. After the completion of dropwise addition, the mixture was stirred for 30 minutes. To this mixture was added dropwise 59.4 g (0.57 mol) of 35% hydrochloric acid to allow sedimentation of white crystals of 4'-methylbiphenyl-2-carboxylic acid. The resulting crystals were collected by filtration, sufficiently washed with 200 ml of water, and then air-dried to give 54.4 g of brownish white crystals of 4'-methylbiphenyl-2-carboxylic acid (yield: 99% based on 2-cyano-4'-methylbiphenyl, purity: 99.0%). Next, the resulting crystals were recrystallized from toluene to give 45.8 g of white crystals (yield: 83.3% based on 2-cyano-4'-methylbiphenyl, purity: 99.9%). The resulting white crystals had a melting point of 150.4° C.

EXAMPLE I-3

A 300-ml four-neck flask equipped with a thermometer and a reflux condenser was charged with 28.99 g of ethylene glycol, 28.99 g of water, 28.99 g (0.15 mol) of 2-cyano-4'-methylbiphenyl and 12.0 g (0.30 mol) of sodium hydroxide, and they were mixed together and then heated.

The resulting reaction solution was stirred at a temperature of 150° C. for 8 hours at a pressure of 1 to 2 kgf/cm$^2$, and then cooled to 90° C. To this reaction solution was added dropwise 28.99 g of water. After the completion of dropwise addition, the mixture was stirred for 30 minutes. To this mixture was added 66.6 g of toluene, and 34.4 g (0.33 mol) of 35% hydrochloric acid was further added dropwise. The temperature inside the flask was raised to 75° C. to dissolve the resulting product in toluene and form into two layers. After the solution was allowed to stand to separate into layers, the lower aqueous layer was removed therefrom. The toluene layer was dehydrated over anhydrous magnesium sulfate, and the solution was then gradually cooled to allow sedimentation of white crystals of 4'-methylbiphenyl-2-carboxylic acid. The temperature was lowered to 0° C., and its temperature was maintained for one hour, and then the crystals were filtered. The crystals were washed with 15 g of toluene at 0° C., and then air-dried to give 28.8 g of white crystals of 4'-methylbiphenyl-2-carboxylic acid (yield: 90.6% based on 2-cyano-4'-methylbiphenyl, purity: 99.9%). The resulting white crystals had a melting point of 150.2° C.

EXAMPLE I-4

A 300-ml four-neck flask equipped with a thermometer and a reflux condenser was charged with 87.9 g of ethylene glycol, 43.5 g (0.244 mol) of 2-cyanobiphenyl and 24.4 g (0.610 mol) of sodium hydroxide, and they were mixed together and then heated.

The reaction solution was stirred at 150° to 155° C. for 16 hours, and then cooled to 90° C. To this reaction solution was added dropwise 175.8 g of water. After the completion of dropwise addition, the mixture was stirred for 30 minutes. To this mixture was added 64 g of toluene, and 69.9 g (0.671 mol) of 35% hydrochloric acid was further added dropwise. The temperature inside the flask was raised to 75° C. to dissolve the resulting product in toluene and form into two layers. After the solution was allowed to stand, and separated into layers, the lower aqueous layer was removed therefrom. The toluene layer was dehydrated over anhydrous magnesium sulfate. Thereafter, to this toluene layer was added 32 g of normal-heptane, and the mixture was treated with activated charcoal. Thereafter, the solution was gradually cooled to allow sedimentation of white crystals of biphenyl-2-carboxylic acid. The temperature was lowered to 0° C., and its temperature was maintained for one hour, and the crystals were filtered. The crystals were washed with 20 g of a mixed solvent of toluene/normal-heptane=2/1 (weight ratio) at 0° C. and then air-dried to give 45.6 g of white crystals of biphenyl-2-carboxylic acid (yield: 94.2% based on 2-cyanobiphenyl, purity: 99.9%). The resulting white crystals had a melting point of 114.9° C.

It can be seen from the above results that biphenyl-2-carboxylic acid having a high purity can be prepared in a high yield from 2-cyano-4'-methylbiphenyl according to the processes in Examples I-1 to I-4.

EXAMPLE II-1

A 100-ml flask was charged with 5 ml of toluene, 0.24 g (2 mmol) of anhydrous magnesium sulfate and 0.11 ml (2 mmol) of concentrated sulfuric acid, and they were vigorously stirred. To this mixture was added 2.12 g (10 mmol) of 4'-methyl-2-biphenylcarboxylic acid, and isobutene gas (98 mmol) was introduced thereto at a flow rate of 1.2 liter/min for 2 minutes. The resulting mixture was stirred at room temperature for 6 hours. After having confirmed that almost all of the peaks ascribed to 4'-methyl-2-biphenylcarboxylic acid disappeared by HPLC, 4 ml of deionized water was poured into the mixture, and sufficiently stirred. Thereafter, the mixture was allowed to stand to separate into layers. The upper toluene layer was taken out therefrom, and the toluene layer was washed with a 1.5 M aqueous sodium hydroxide, and dried over anhydrous magnesium sulfate. Thereafter, the toluene layer was concentrated by distilling off toluene by using a rotary evaporator, to give 2.54 g of tert-butyl 4'-methyl-2-biphenylcarboxylate as crystals (yield: 95% based on 4'-methyl-2-biphenylcarboxylic acid, purity by HPLC: 99.9%).

Incidentally, the obtained compound was identified as tert-butyl 4'-methyl-2-biphenylcarboxylate by the following physical properties:

(1) Melting point: 51°–53° C.

(2) IR (neat) ν(cm$^{-1}$): 2976, 2928, 1708, 1478, 1446, 1368, 1302, 1250, 1174, 1128, 848, 820, 760.

(3) $^1$H-NMR (CDCl$_3$) δ (ppm): 7.08–7.74 (m, 8H), 2.34 (s, 3H), 1.27 (s, 9H).

EXAMPLE II-2

A 100-ml flask was charged with 5 ml of toluene and 2.12 g (10 mmol) of 4'-methyl-2-biphenylcarboxylic acid, and they were vigorously stirred. To this mixture was added 0.32 ml (5 mmol) of methanesulfonic acid, and isobutene gas (98 mmol) was introduced thereto at a flow rate of 1.2 liter/min for 2 minutes. The resulting mixture was stirred at room temperature for 20 minutes. After having confirmed that almost all of the peaks ascribed to 4'-methyl-2-biphenylcarboxylic acid disappeared by HPLC, the reaction solution was washed with a 1.5 M aqueous sodium hydroxide, and dried over anhydrous magnesium sulfate. Thereafter, the solution was concentrated by distilling off toluene by using a rotary evaporator, to give 2.52 g of tert-butyl 4'-methyl-2-biphenylcarboxylate as crystals (yield: 94% based on 4'-methyl-2-biphenylcarboxylic acid, purity by HPLC: 99.9%). Incidentally, the obtained compound had the same physical properties as those of the compound obtained in Example II-1.

EXAMPLE II-3

A 100-ml flask was charged with 5 ml of toluene and 2.12 g (10 mmol) of 4'-methyl-2-biphenylcarboxylic acid, and they were vigorously stirred. To this mixture was added dropwise 0.18 ml (2 mmol) of phosphorus oxytrichloride, and isobutene gas (98 mmol) was introduced to the mixture at a flow rate of 1.2 liter/min for 2 minutes. The resulting mixture was stirred at room temperature for 6 hours. After having confirmed that almost all of the peaks ascribed to 4'-methyl-2-biphenylcarboxylic acid disappeared by HPLC, the reaction solution was washed with a 1.5 M aqueous sodium hydroxide. The reaction solution was dried over anhydrous magnesium sulfate, and then the mixture was concentrated by distilling off toluene by using a rotary evaporator, to give 2.63 g of tert-butyl 4'-methyl-2-biphenylcarboxylate as crystals (yield: 98% based on 4'-methyl-2-biphenylcarboxylic acid, purity by HPLC: 99.9%). Incidentally, the obtained compound had the same physical properties as those of the compound obtained in Example II-1.

EXAMPLE II-4

A 500-ml flask was charged with 50 ml of toluene and 53.42 g (0.25 mol) of 4'-methyl-2-biphenylcarboxylic acid, 0.45 ml (0.025 mol) of water and 32.63 g (0.58 mol) of isobutene. To this mixture was added dropwise 7.74 g (0.05 mol) of phosphorus oxytrichloride, and the mixture was stirred for 6 hours. The reaction mixture was added to 50 ml of a 10%-aqueous sodium hydroxide and washed. The organic layer was dried over anhydrous magnesium sulfate. Thereafter, the organic layer was concentrated by distilling off toluene by using a rotary evaporator, to give 64.2 g of tert-butyl 4'-methyl-2-biphenylcarboxylate as crystals (yield: 95% based on 4'-methyl-2-biphenylcarboxylic acid, purity by HPLC: 99.9%). Incidentally, the obtained compound had the same physical properties as those of the compound obtained in Example II-1.

It can be seen from the above results that tert-butyl 4'-methyl-2-biphenylcarboxylate having high quality can be conveniently prepared in a high yield according to the processes in Examples II-1 to II-4.

As explained above, according to the present invention, tert-butyl 4'-methyl-2-biphenylcarboxylate having high quality can be conveniently and industrially advantageously prepared in a high yield under mild reaction conditions such as ambient temperatures without complicated procedures or any hazardous solvents.

INDUSTRIAL APPLICABILITY tert-Butyl 4'-methyl-2-biphenylcarboxylate obtained by the process of the present invention can be preferably used as intermediates of antihypertensives.

What is claimed is:

1. A process for preparing tert-butyl 4'-methyl-2-biphenylcarboxylate comprising reacting 4'-methyl-2-biphenylcarboxylic acid with isobutene in a hydrocarbon solvent or a halogenated solvent in the presence of an acid catalyst selected from the group consisting of sulfuric acid, a sulfonic acid and a phosphorus halide, with the proviso that 4'-methyl-2-biphenylcarboxylic acid is reacted with isobutene in the presence of a dehydrating agent when sulfuric acid is used as the acid catalyst.

2. The process according to claim 1, wherein the phosphorus halide is phosphorus oxytrichloride.

3. The process according to claim 1, wherein the dehydrating agent is anhydrous magnesium sulfate.

4. The process according to claim 1, wherein the hydrocarbon solvent is cyclohexane or toluene.

5. The process according to claim 1, wherein the halogenated solvent is dichloromethane or dichloroethane.

6. The process according to claim 1, wherein 4'-methyl-2-biphenylcarboxylic acid is prepared by hydrolyzing 2-cyano-4'-methylbiphenyl under normal pressure to 10 $kgf/cm^2$ in a glycol in the presence of an alkali.

* * * * *

UNITED STATES PATENT AND TRADEMARK OFFICE
CERTIFICATE OF CORRECTION

PATENT NO. : 6,369,266 B1
DATED : April 9, 2002
INVENTOR(S) : Shintaku et al.

It is certified that error appears in the above-identified patent and that said Letters Patent is hereby corrected as shown below:

<u>Title page,</u>
Please add the following information:
-- [22]  PCT Filed: November 13, 1998 --

-- [86]  PCT No.: PCT/JP98/05099
    § 371 (c )(1),
     (2), (4) Date: May 8, 2000 --

-- [87]  PCT Pub. No.: WO99/25679
    PCT Pub Date: May 27, 1999 --

Item [54], Title, please delete "PROCESS FOR PRODUCING TERT-BUTYL 4'-METHYL-2-BIPHENYLCARBOXLATE" and insert -- PROCESS FOR PRODUCING TERT-BUTYL 4'-METHYL-2-BIPHENYLCARBOXYLATE --

Signed and Sealed this

Seventeenth Day of December, 2002

JAMES E. ROGAN
*Director of the United States Patent and Trademark Office*